US007641092B2

(12) United States Patent
Kruszynski et al.

(10) Patent No.: US 7,641,092 B2
(45) Date of Patent: Jan. 5, 2010

(54) SWING GATE FOR DEVICE LOCKOUT IN A CURVED CUTTER STAPLER

(75) Inventors: Michael L. Kruszynski, Loveland, OH (US); Michael R. Ludzack, Maineville, OH (US); William D. Kelly, Mason, OH (US); Howard N. Flaxman, McLean, VA (US)

(73) Assignee: Ethicon Endo - Surgery, Inc., Cincinnati, OH (US)

( * ) Notice: Subject to any disclaimer, the term of this patent is extended or adjusted under 35 U.S.C. 154(b) by 38 days.

(21) Appl. No.: 11/197,520

(22) Filed: Aug. 5, 2005

(65) Prior Publication Data

US 2007/0029364 A1 Feb. 8, 2007

(51) Int. Cl.
*A61B 17/10* (2006.01)
(52) U.S. Cl. .............. 227/175.2; 227/176.1; 227/175.4; 227/19; 227/178.1
(58) Field of Classification Search .............. 227/176.1, 227/175.2, 175.4, 178.1, 19
See application file for complete search history.

(56) References Cited

U.S. PATENT DOCUMENTS

| | | | | |
|---|---|---|---|---|
| 4,892,244 A * | 1/1990 | Fox et al. | ................. | 227/175.4 |
| 5,071,052 A * | 12/1991 | Rodak et al. | ............. | 227/175.2 |
| 5,413,267 A * | 5/1995 | Solyntjes et al. | ......... | 227/175.4 |
| 5,462,215 A * | 10/1995 | Viola et al. | ............... | 227/176.1 |
| 5,470,006 A | 11/1995 | Rodak | | |
| 5,470,009 A * | 11/1995 | Rodak | ...................... | 227/176.1 |
| 5,673,842 A * | 10/1997 | Bittner et al. | ............. | 227/175.4 |
| 5,706,998 A * | 1/1998 | Plyley et al. | .............. | 227/175.3 |
| 5,735,445 A | 4/1998 | Vidal et al. | | |
| 5,894,979 A * | 4/1999 | Powell | ...................... | 227/175.2 |
| 5,964,394 A * | 10/1999 | Robertson | ................ | 227/176.1 |
| 6,817,508 B1 * | 11/2004 | Racenet et al. | ........... | 227/176.1 |
| 6,988,650 B2 * | 1/2006 | Schwemberger et al. | . | 227/176.1 |

FOREIGN PATENT DOCUMENTS

EP 0537572 4/1993
EP 1550413 7/2005

* cited by examiner

*Primary Examiner*—Rinaldi I. Rada
*Assistant Examiner*—Michelle Lopez
(74) *Attorney, Agent, or Firm*—Welsh + Flaxman LLC

(57) ABSTRACT

A linear surgical stapler adapted for applying a plurality of surgical fasteners to body tissue includes an anvil structure and a cartridge housing containing a plurality of surgical fasteners. The cartridge housing and anvil structure are relatively movable between a first spaced apart position and a second position in close approximation with one another. A firing mechanism is associated with the cartridge housing for ejecting the surgical fasteners from the cartridge housing to be driven against the anvil structure. A lockout mechanism interacts with the cartridge housing for selective activation and deactivation. The lockout mechanism includes a swing gate tab secured to the cartridge housing at a position adjacent a lockout lever, such that firing of the linear surgical stapler rotates the swing gate tab releasing the lockout lever for preventing further firing of the used cartridge housing.

15 Claims, 11 Drawing Sheets

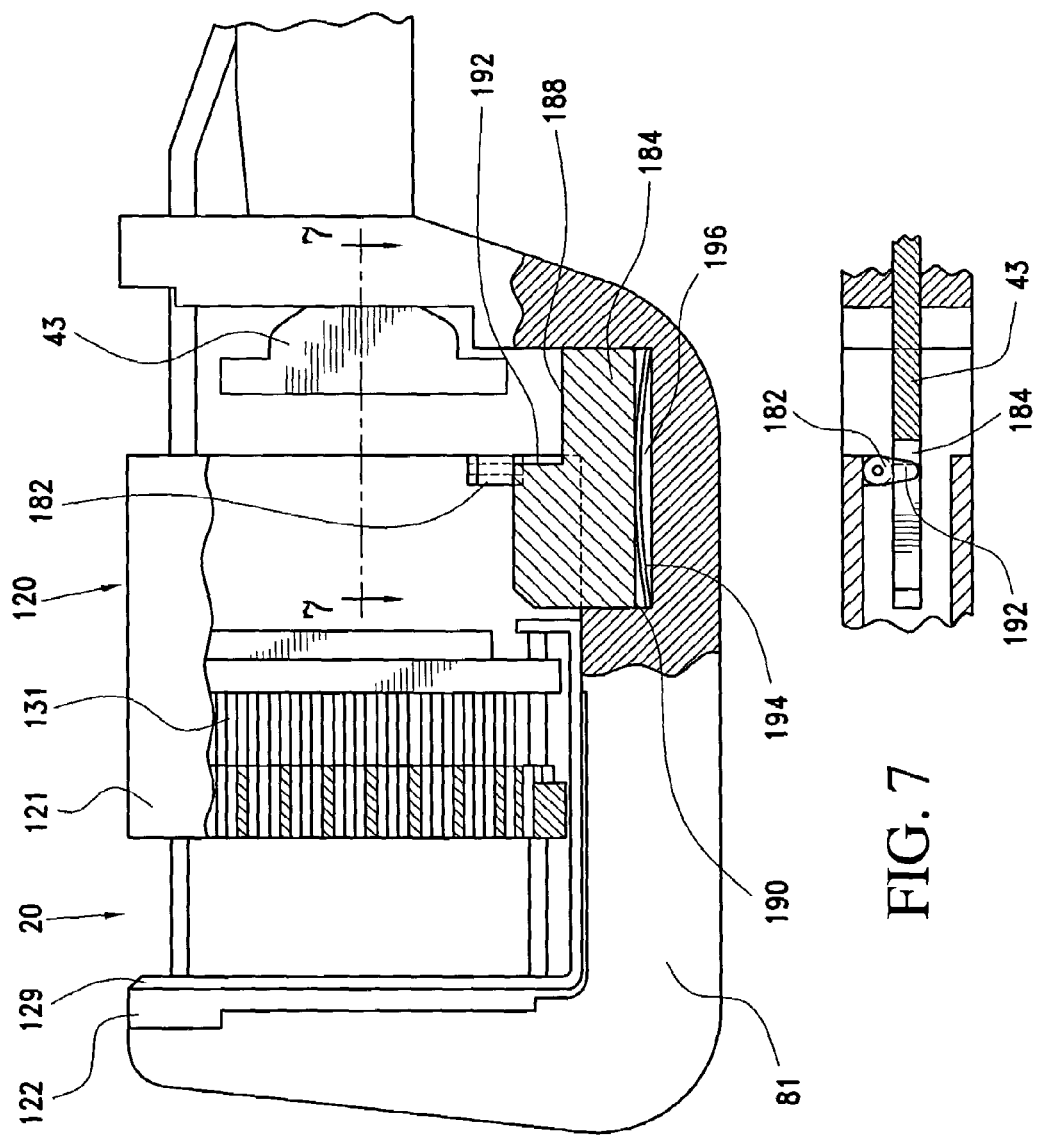

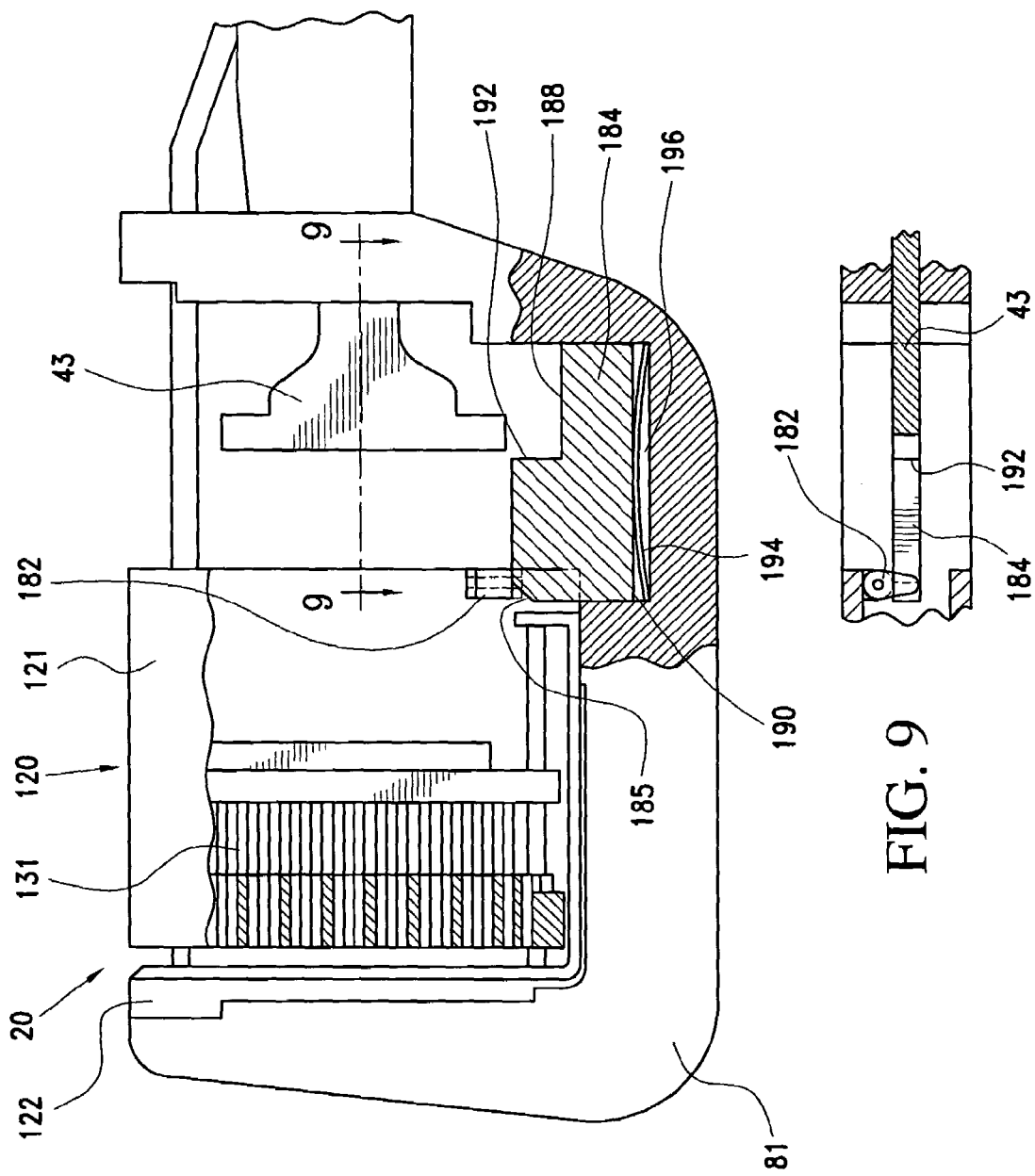

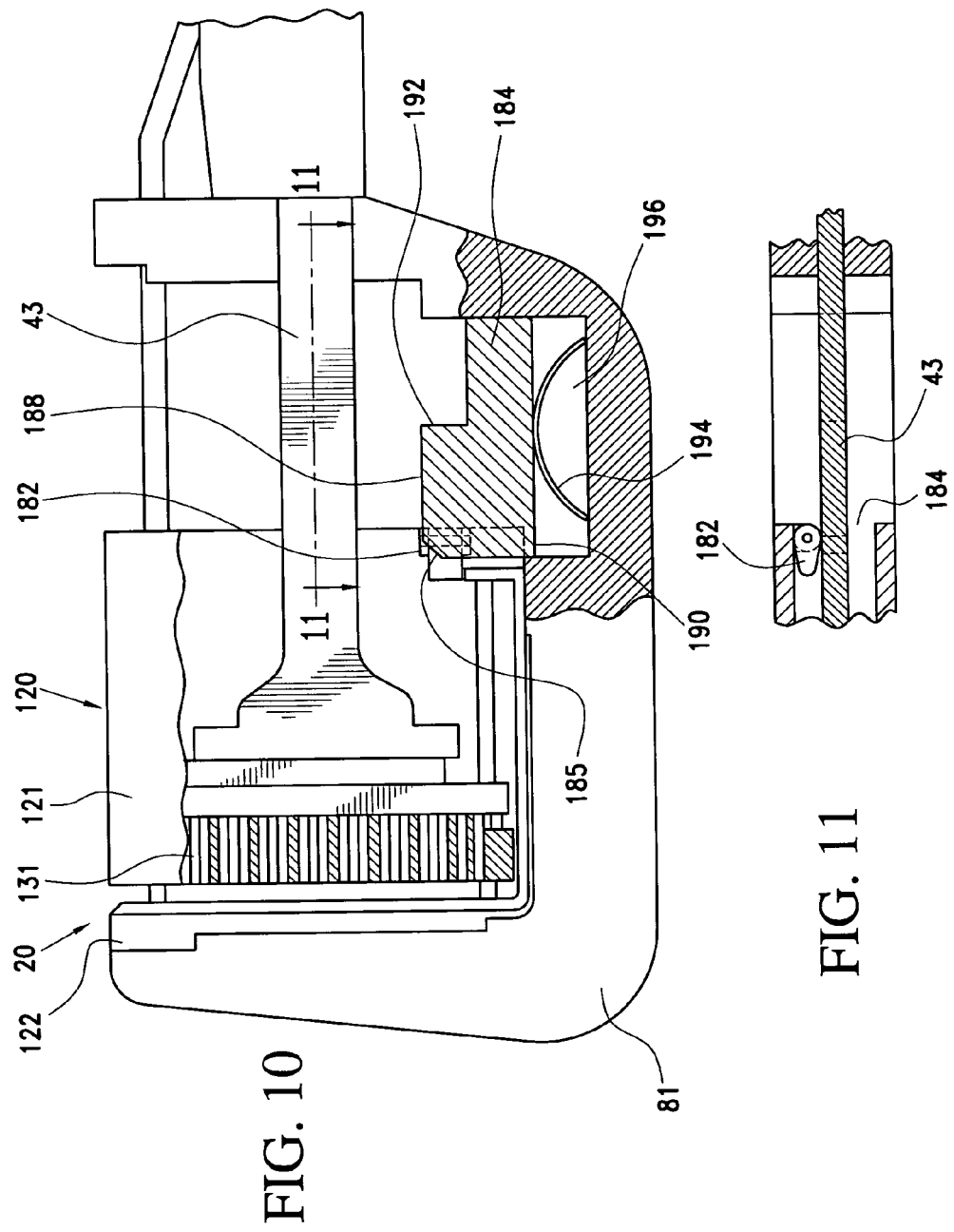

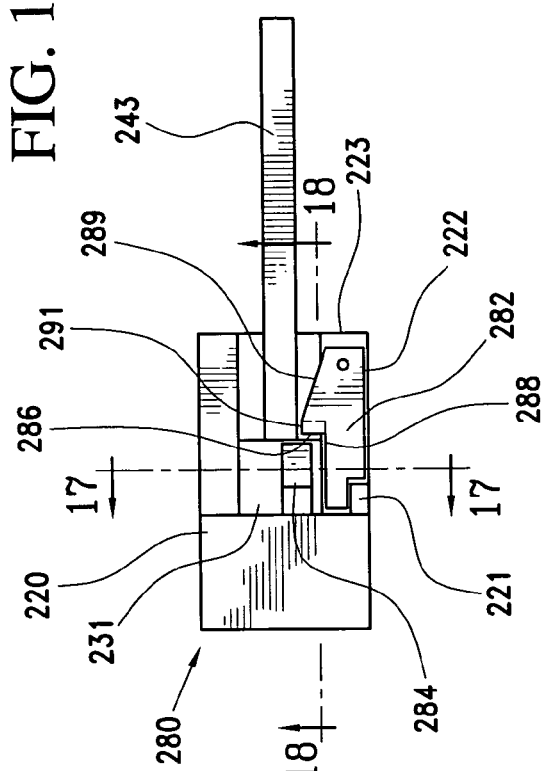
FIG. 15
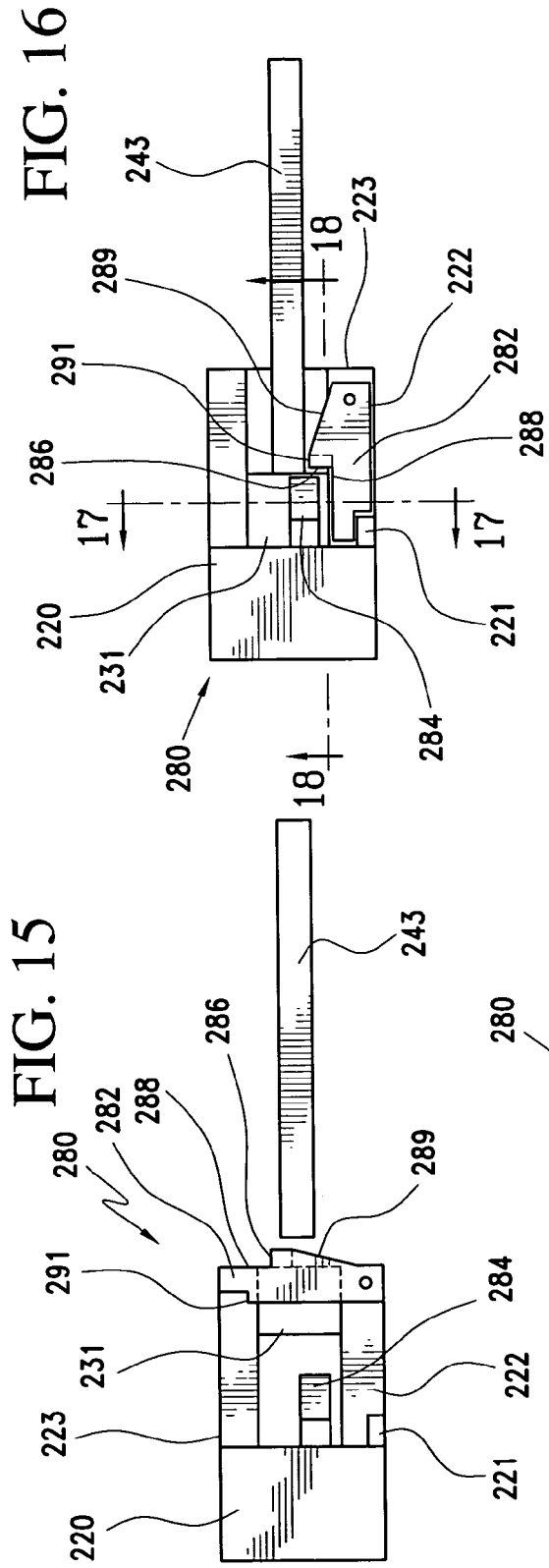
FIG. 16
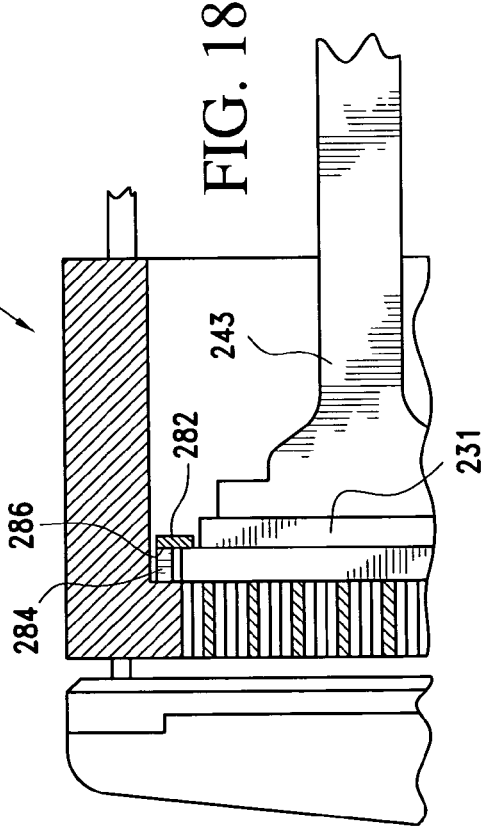
FIG. 17
FIG. 18

SWING GATE FOR DEVICE LOCKOUT IN A CURVED CUTTER STAPLER

BACKGROUND OF THE INVENTION

1. Field of the Invention

The present invention relates to surgical stapling and cutting instruments adapted for use in the diagnosis and therapy of pathologies treated by stapled resection. More particularly, the invention relates to a lockout mechanism for utilization in conjunction with surgical stapling and cutting instruments.

2. Description of the Prior Art

Surgical stapling and cutting instruments are commonly utilized in the diagnosis and treatment of pathologies treated by stapled resection. Surgical stapling and cutting instruments provide a mechanism to extend the transluminal exploitation of mechanical suturing devices introduced via the anal canal, mouth, stomach and service accesses. Although surgical stapling and cutting instruments are most commonly utilized with rectal pathologies, surgical stapling and cutting instruments may be used in a variety of environments.

Over time, surgical stapling and cutting instruments have been developed. These instruments generally include a support frame, an anvil attached to the support frame and a cartridge housing carrying a plurality of staples. The instruments also include a driver within the cartridge housing which pushes all of the staples out simultaneously into the anvil to form the staples into a generally B-shape, suturing tissue together. In addition, these instruments include approximation mechanisms that allow for the cartridge housing and anvil to move relative to each other to accept tissue therebetween. Finally, the instruments include a firing mechanism for moving the driver forward to form the staples against the anvil.

In addition to the basic components of the stapling and cutting instruments, these products need a lockout mechanism permitting activation and/or deactivation of the firing means such that the cartridge module may be utilized as a clamp when needed during an emergency. However, the lockout mechanism is designed such that the firing mechanism only works for a cartridge module that has not been previously used.

Current surgical stapling instruments include a firing bar lockout that is activated by the driver. When a new cartridge module is loaded into the instrument, the location of the driver, as it relates to the cartridge module in the instrument, interferes with the lockout arm in a way so as to let the instrument fire staples. After the instrument fires staples, the location of the driver moves distally in a way that it no longer interferes with the lockout arm. The lockout arm moves to a position that now interferes with the firing bar, but prevents the firing bar from moving distally. However, prior art lockout mechanism include shortcoming which the present invention attempts to overcome.

In particular, prior art devices allow the driver to be pushed back in a manner which could result in turning off the lockout as they tend to be dependent upon the position of the driver in relation to the lockout mechanism. These products, if the driver was pushed back far enough to visually hide the driver in the cartridge, would no longer provide the user a visual indicator of a spent cartridge. In addition, some prior art lockout mechanisms do not provide a strong lockout due to the components interacting in creating the lockout after firing. As such, a need exists for an improved lockout mechanism that provides a clear indication that the lockout mechanism has been activated and overcomes the other shortcomings of prior art lockout mechanisms. The present invention provides such a lockout mechanism.

SUMMARY OF THE INVENTION

It is, therefore, an object of the present invention to provide a linear surgical stapler adapted for applying a plurality of surgical fasteners to body tissue. The surgical stapler includes an anvil structure and a cartridge housing containing a plurality of surgical fasteners. The cartridge housing and anvil structure are relatively movable between a first spaced apart position and a second position in close approximation with one another. A firing mechanism is associated with the cartridge housing for ejecting the surgical fasteners from the cartridge housing to be driven against the anvil structure. A lockout mechanism interacts with the cartridge housing for selective activation and deactivation. The lockout mechanism includes a swing gate tab secured to the cartridge housing at a position adjacent a lockout lever, such that firing of the linear surgical stapler rotates the swing gate tab releasing the lockout lever for preventing further firing of the used cartridge housing.

It is also an object of the present invention to provide a linear surgical stapler wherein the lockout lever is spring biased.

It is another object of the present invention to provide a linear surgical stapler wherein the lockout lever is mounted on a support frame of the linear surgical stapler adjacent the cartridge housing.

It is a further object of the present invention to provide a linear surgical stapler wherein the lockout lever sits within a recess formed in the support frame of the linear surgical stapler.

It is also another object of the present invention to provide a linear surgical stapler wherein the lockout lever includes a top surface exposed from the recess and a lower surface sitting within the recess.

It is still another object of the present invention to provide a linear surgical stapler wherein the top surface includes a tab member shaped and dimensioned for engaging the firing mechanism in a manner preventing firing of the present linear surgical stapler.

It is yet a further object of the present invention to provide a linear surgical stapler wherein the swing gate tab is pivotally secured to the cartridge housing such that it sits above the lockout lever when it is positioned for locking of the lockout lever prior to firing of the linear surgical stapler.

It is also an object of the present invention to provide a linear surgical stapler wherein the swing gate tab moves between a first position substantially transverse to a longitudinal axis of the linear surgical stapler and a second position substantially parallel to the longitudinal axis of the linear surgical stapler, the swing gate tab sits above the lockout lever in its first position holding down the lockout lever in an unlocked positioned.

It is another object of the present invention to provide a linear surgical stapler wherein prior to firing of the linear surgical stapler the swing gate tab is positioned slightly forward of the lockout lever such that rotation of the swing gate tab causes the swing gate tab to come into contact with the lockout lever.

It is a further object of the present invention to provide a linear surgical stapler wherein the swing gate tab moves between a first position substantially transverse to a longitudinal axis of the linear surgical stapler and a second position substantially parallel to the longitudinal axis of the linear surgical stapler, such that when the swing gate tab is in its first position it sits forward of an upper surface of the lockout lever and during firing of the surgical stapler device the swing gate tab is rotated to its second position substantially parallel to the longitudinal axis of the surgical stapler device and removed from the upper surface of the lockout lever permitting the lockout lever to move upwardly into a locked position.

It is also an object of the present invention to provide a linear surgical stapler wherein force from the firing mechanism rotates the swing gate tab with enough force to deflect the lockout lever downwardly into the recess and out of the way of the firing bar and movement of the swing gate tab continues to its second position substantially parallel to the longitudinal axis of the surgical stapling device where, and once the firing mechanism is retracted, the lockout lever returns to a blocking position preventing any further rotation of the swing gate and firing of the linear surgical stapler.

It is another object of the present invention to provide a linear surgical stapler which includes an anvil structure and a cartridge housing containing a plurality of surgical fasteners. The cartridge housing and anvil structure are relatively movable between a first spaced apart position and a second position in close approximation with one another. A firing mechanism is associated with the cartridge housing for ejecting the surgical fasteners from the cartridge housing to be driven against the anvil structure. A lockout mechanism interacts with the cartridge housing for selective activation and deactivation. The lockout mechanism includes a swing gate pivotally secured to the cartridge housing such that firing of the linear surgical stapler rotates the swing gate for preventing further firing of the used cartridge housing.

It is a further object of the present invention to provide a linear surgical stapler wherein a front facing surface of the swing gate includes a cut out section positioned for engaging a driver of the stapler and preventing further movement thereof.

It is also an object of the present invention to provide a linear surgical stapler including a lock tab which prevents movement of the swing gate after rotation of the swing gate during firing.

It is another object of the present invention to provide a linear surgical stapler wherein the swing gate is mounted along a side wall of the cartridge housing.

Other objects and advantages of the present invention will become apparent from the following detailed description when viewed in conjunction with the accompanying drawings, which set forth certain embodiments of the invention.

BRIEF DESCRIPTION OF THE DRAWINGS

FIGS. 6 through 13 show the various steps involved in the actuation of the lockout mechanism used with the present linear surgical stapler.

FIGS. 15, 16, 17 and 18 show an alternate lockout mechanism in accordance with the present invention.

DESCRIPTION OF THE PREFERRED EMBODIMENTS

Figure 1:
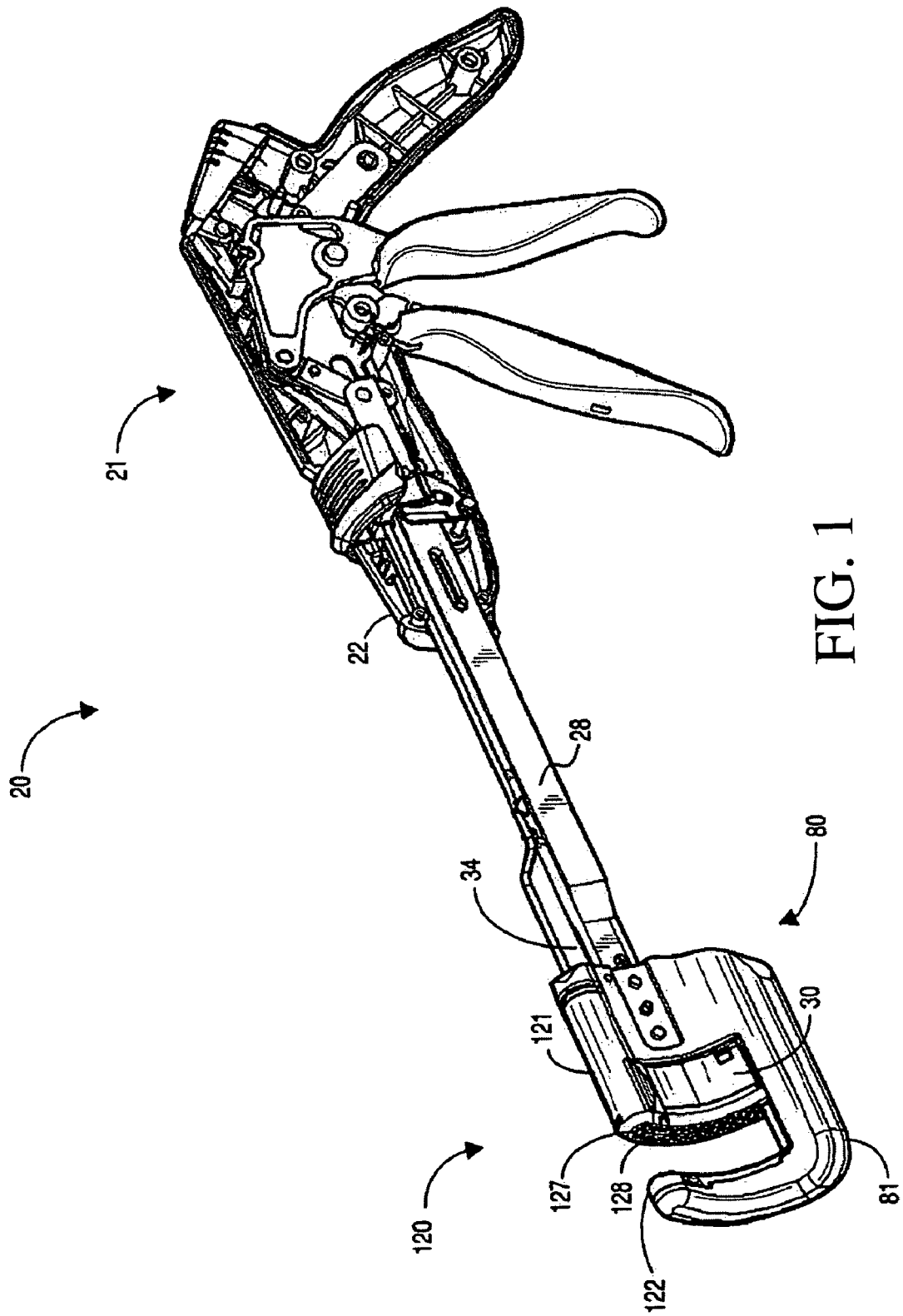
FIG. 1 is a perspective view of the linear surgical stapler in accordance with the present invention.
Figure 2:
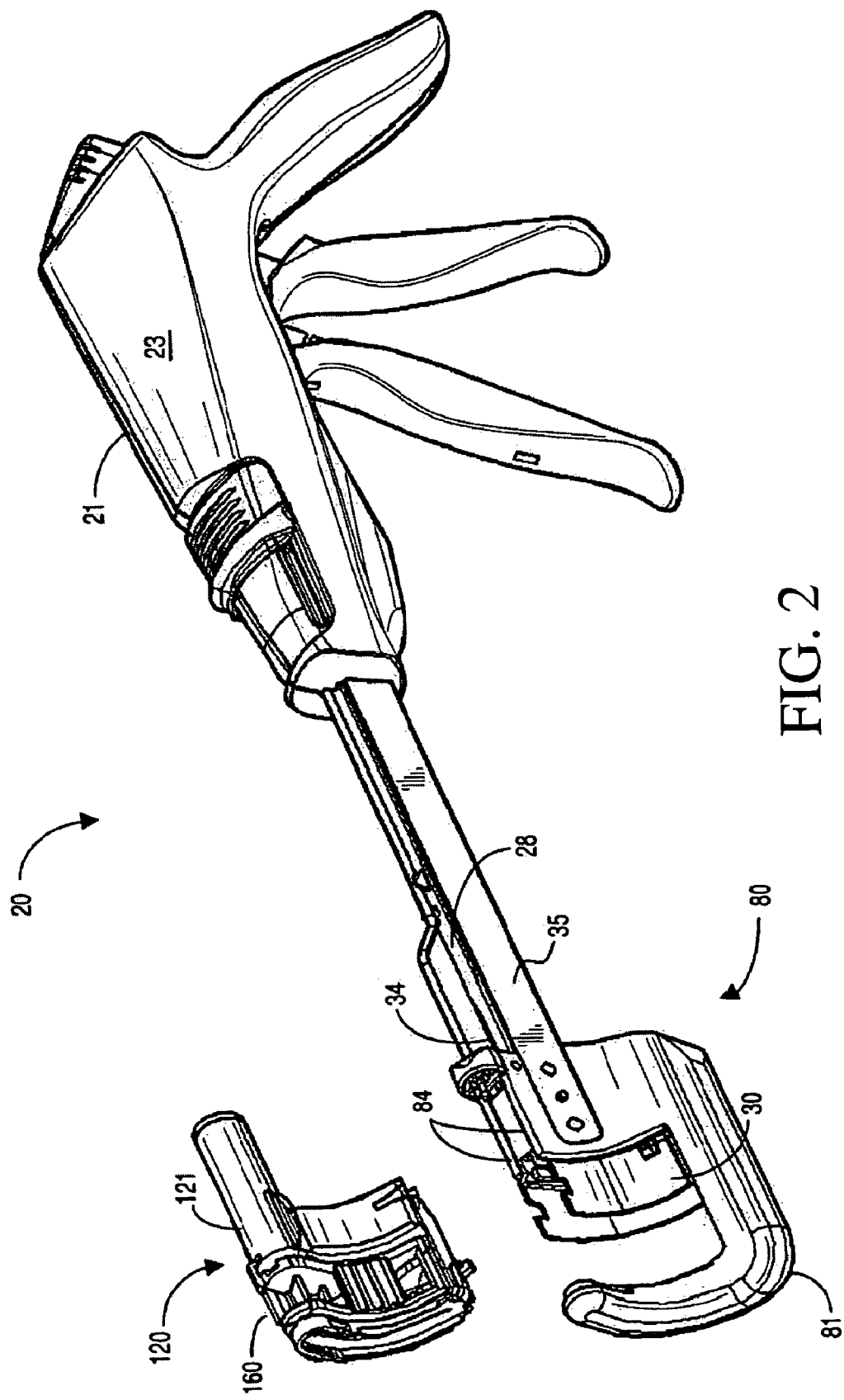
FIG. 2 is perspective view of the linear surgical stapler with the cartridge module removed.
Figure 3:
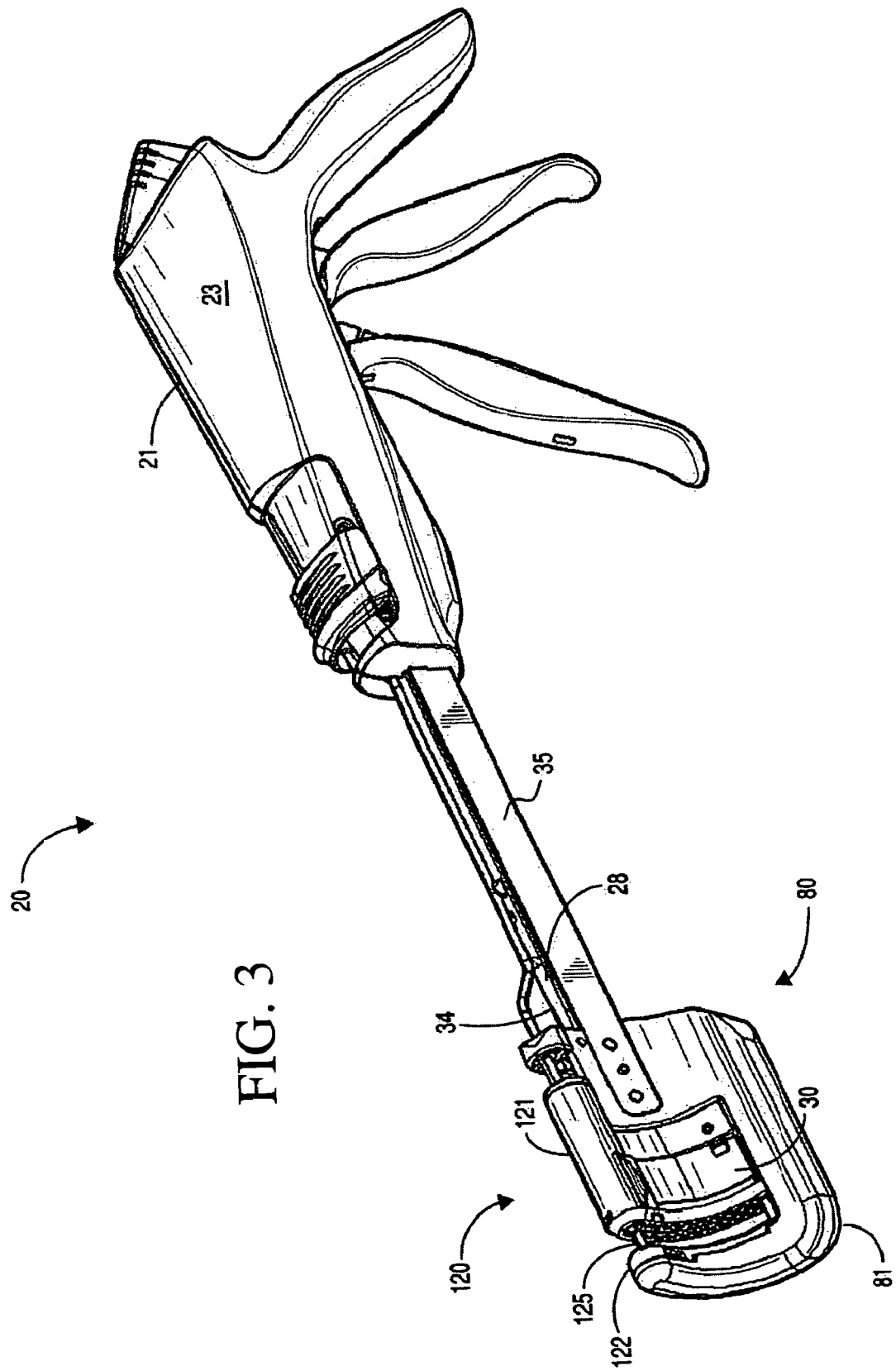
FIG. 3 is a perspective view of the linear surgical stapler with the cartridge housing moved to an intermediate position.
Figure 4:
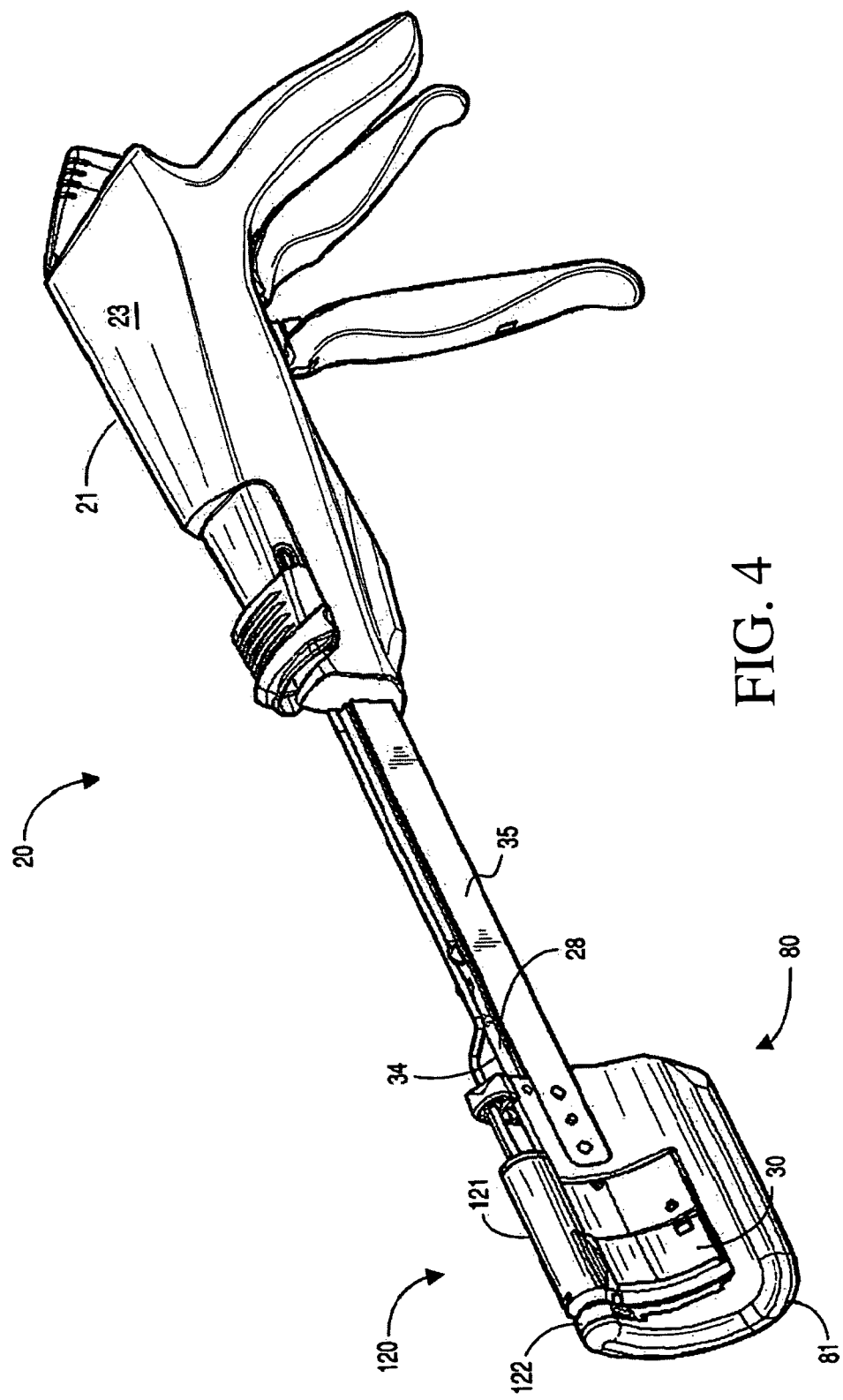
FIG. 4 is a perspective view of the linear surgical stapler with the cartridge housing moved to a closed position.
Figure 5:
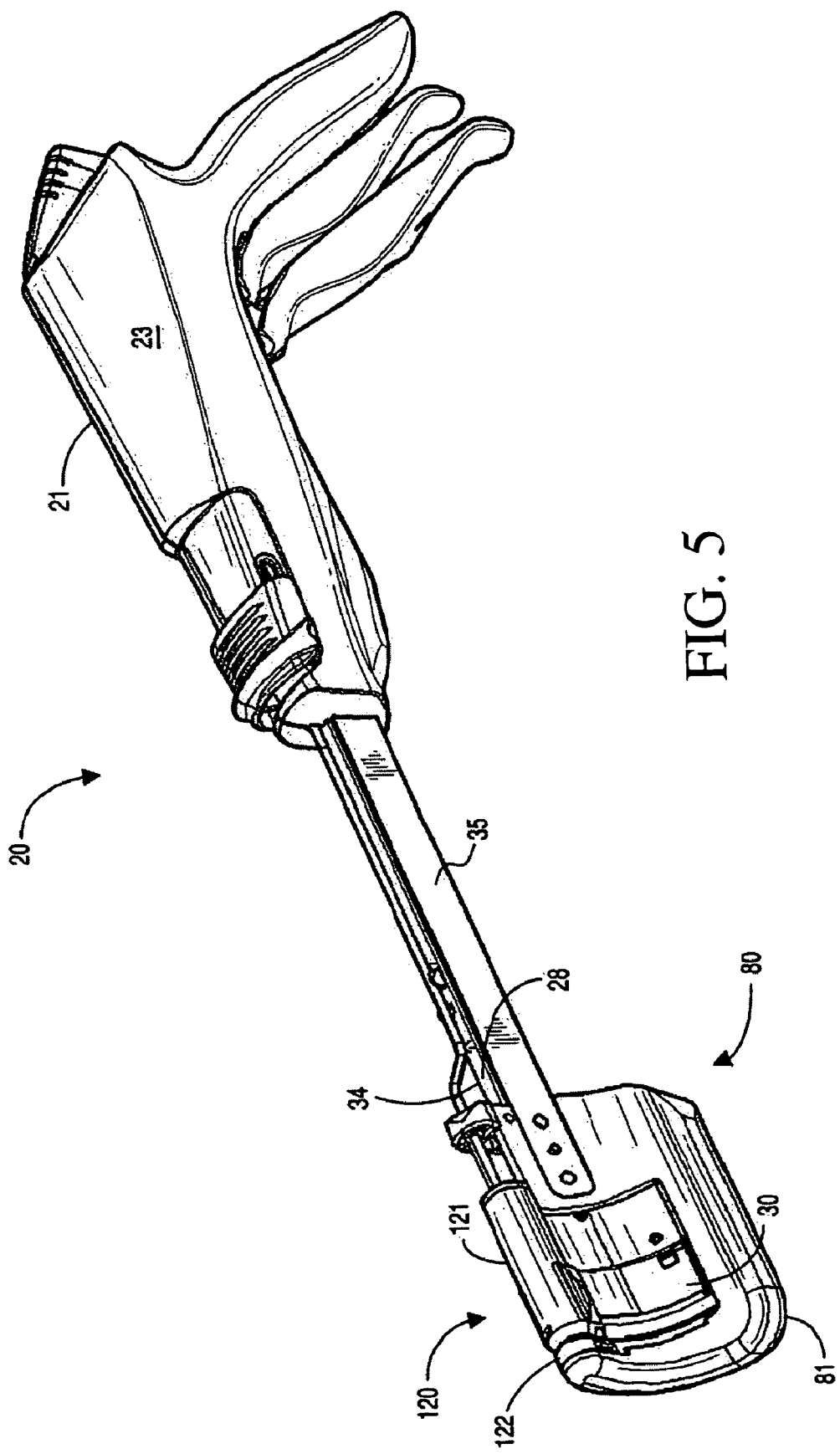
FIG. 5 is a perspective view of the linear surgical stapler with the firing trigger in a firing position.
Figures 12, 13:
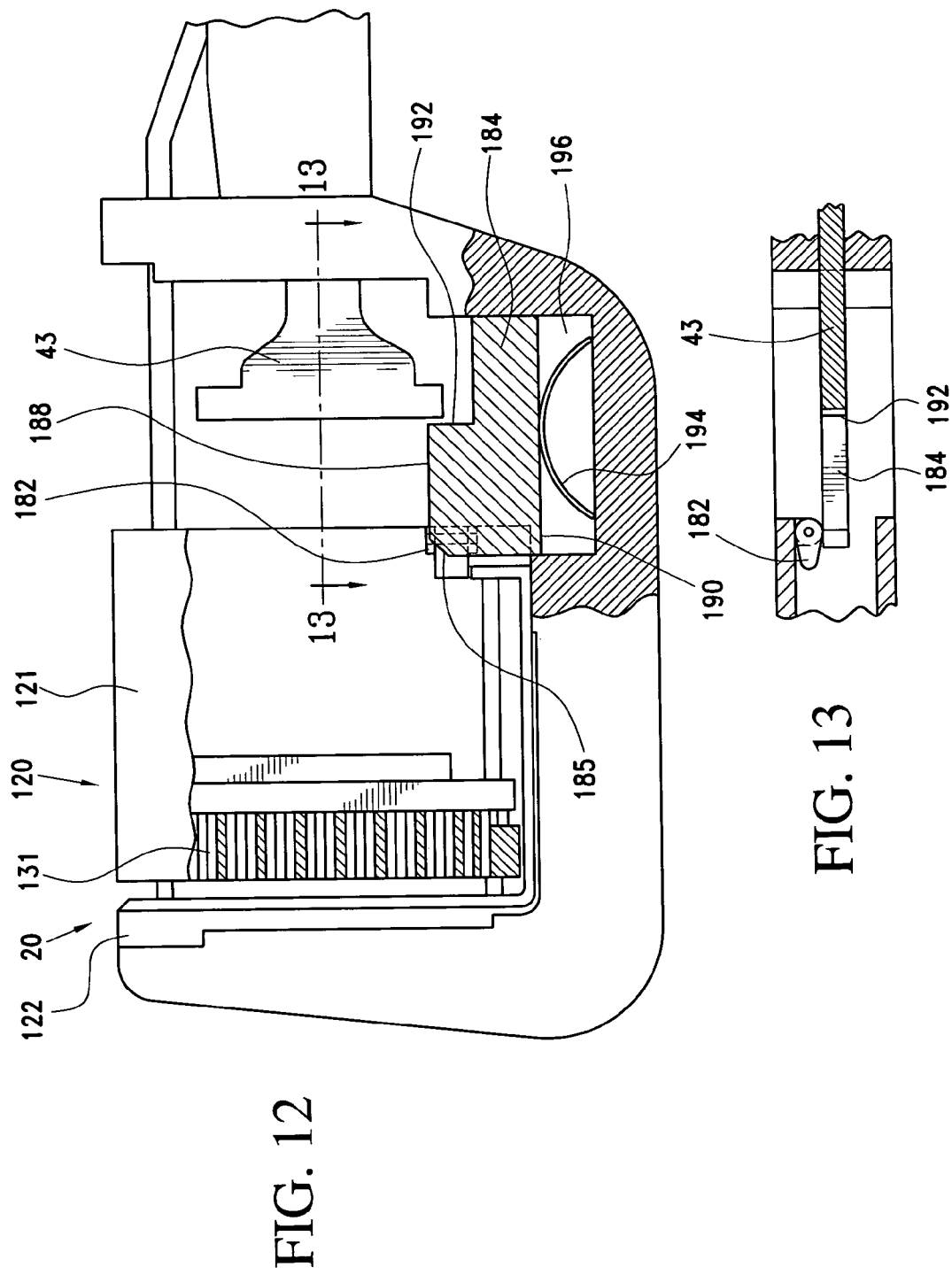

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as the basis for the claims and as a basis for teaching one skilled in the art how to make and/or use the invention.

With reference to the various figures, a surgical instrument 20 adapted for applying a plurality of surgical fasteners to body tissue is disclosed. The surgical instrument 20 includes an anvil 122 and a cartridge housing 121 containing a plurality of surgical fasteners. The cartridge housing 121 and anvil 122 are relatively movable between a first spaced apart position and a second position in close approximation with one another. A firing mechanism is associated with the cartridge housing 121 for ejecting the surgical fasteners from the cartridge housing 121 to be driven against the anvil 122. The lockout mechanism 180 includes a swing gate tab 182 secured to the cartridge housing 120 at a position adjacent a lockout lever 184, such that firing of the linear surgical stapler 20 rotates the swing gate tab 182 releasing the lockout lever 184 for preventing further firing of the used cartridge housing 120.

Referring to FIG. 1 in combination with FIGS. 2 to 5, there is shown a surgical stapling and cutting instrument, in particular, a linear surgical stapler 20 which is designed to staple and cut tissue. The linear surgical stapler 20 has a handle 21 at a first proximal end and an end effector 80 at an opposite distal end. The end effector 80 is curved in accordance with a preferred embodiment of the present invention. Right and left hand structural plates (often called "handle plates") 34, 35, respectively, connect the handle 21 to the end effector 80 of the instrument (the left hand handle plate is not shown in FIG. 1). The handle 21 has a right hand shroud 22 coupled to a left hand shroud (the left hand shroud is not shown in FIG. 1). The handle 21 also has a body portion 23 to grip and maneuver the linear surgical stapler 20 (see FIG. 2 to 5).

The end effector 80 is a surgical fastening assembly that includes a cartridge module 120 and a C-shaped supporting structure 81. The term C-shaped is used throughout the specification to describe the concave nature of the supporting structure 81 and the cartridge module 120. The C-shaped construction facilitates enhanced functionality and the use of the term C-shaped in the present specification should be construed to include a variety of concave shapes which would similarly enhance the functionality of surgical stapling and cutting instruments. Although a C-shaped construction is contemplated in accordance with a preferred embodiment of the present invention, those skilled in the art will appreciate the supporting structure may take various shapes without departing from the spirit of the present invention. The distal end 30 of a closure member 28 is disposed to receive the cartridge module 120. The end effector 80 also includes a safety lockout mechanism 180 (best seen in FIGS. 6 to 13) for preventing the firing of a previously fired cartridge module 120. The cartridge module 120 contains a cartridge housing 121 coupled to an anvil 122. The cartridge module 120 also includes a retaining pin 125, a knife 126, a removable retainer 160, a tissue contacting surface 127 which displays a plurality of staple-containing slots 128 in staggered formation in one or more rows (that is, staple lines) on either side of the knife 126. Staples (not shown) are fired from the cartridge housing 121 against staple-forming surface 129 of the anvil 122 that faces the tissue-contacting surface 127 of the cartridge housing 121.

As will become apparent based upon the following disclosure, the present linear surgical stapler 20 is designed as a multiple firing device with a replaceable cartridge module 120. However, it should be understood that many of the underlying concepts of the present invention may be equally applied in single firing devices without departing from the spirit of the present invention. With this in mind, operation of components other than the lockout mechanism are disclosed in commonly owned U.S. patent Ser. No. 11/014,910, entitled "CURVED CUTTER STAPLER SHAPED FOR MALE PELVIS", filed Dec. 20, 2004, which is incorporated herein by reference.

Referring to FIGS. 6 though 13 (cut away view into cartridge and support structure), the components of the fired device lockout mechanism 180 will now be described. The fired device lockout mechanism 180 in accordance with the present invention employs a swing gate tab 182 secured to the unused cartridge module 120 at a positioned adjacent a spring biased lockout lever 184. More specifically, the swing gate tab 182 is shaped and dimensioned for positioning above the lockout lever 184 to prevent upward movement of the lockout lever 184 to a locking position in which it prevents forward movement of the firing bar 43. With this in mind, and prior to firing of the firing bar 43, the swing gate tab 182 is positioned directly above the lockout lever 184 such that it counters the spring bias urging the lockout lever 184 to a locking position.

More specifically, the lockout lever 184 is mounted on the supporting structure 81 of the linear surgical stapler 20. The lockout lever 184 sits within a recess 196 formed in the supporting structure 81 of the linear surgical stapler 20. The lockout lever 184 includes a top surface 188 exposed from the recess 196 and a lower surface 190 sitting within the recess 196. The top surface 188 includes a tab member 192 shaped and dimensioned for engaging the firing bar 43 in a manner which will be discussed below in greater detail. A spring 194 is positioned between the lower surface 190 and the recess 196. The spring 194 functions to urge the lockout lever 184 upwardly to a locking positioned in line with the firing part the firing bar 43.

The swing gate tab 182 is pivotally secured to the cartridge module 120 such that it sits above lockout lever 184 when it is positioned for locking of the lockout lever 184 within the recess 196 countering the force of the spring 194. That is, and as will be described below in greater detail, the swing gate tab 182 moves between a first position substantially transverse to the longitudinal axis of the linear surgical stapler 20 and a second position substantially parallel to the longitudinal axis of the linear surgical stapler 20. While the swing gate tab 182 is in its first position, it sits above the upper surface 188 of the lockout lever 184 and holds down the lockout lever 184 in its unlocked positioned. During firing of the linear surgical stapler 20, the swing gate tab 182 is rotated to its second position substantially parallel to the longitudinal axis of the linear surgical stapler 20 and removed from the upper surface 188 of the lockout lever 184 permitting the spring 194 to force the lockout lever 184 upwardly into its locked position.

FIGS. 6 and 7 show the lockout mechanism 180 at the beginning of its cycle. The swing gate tab 182 is in its first position substantially transverse to the longitudinal axis of the surgical stapling device 20. The swing gate tab 182 sits directly over the lockout lever 184 holding the lockout lever 184 within the recess 196 such that it does not interfere with firing of the linear surgical stapler 20, and particularly, the firing bar 43.

When the approximation mechanism is activated as shown in FIGS. 8 and 9, that is, activation of the closure trigger 26, the cartridge housing 121 is advanced to the fully closed position. However, the swing gate tab 182 remains substantially transverse to the longitudinal axis of the linear surgical stapler 20, holding the lockout lever 184 within the recess 196 in its unlocked position.

Referring to FIGS. 10 and 11, activation of the firing transmission assembly advances the firing bar 43 through the swing gate tab 182. Movement of the firing bar 43 through swing gate tab 182 occurs regardless of the position of the driver 131 or completion of the firing stroke. This movement of the firing bar 43 through the swing gate tab 182 moves the swing gate tab 182 from its first position preventing the spring loaded lockout lever 184 from moving upward to its second position substantially parallel to the longitudinal axis for of the linear surgical stapler 20. When in its second position, the swing gate tab 182 is no longer positioned above the upper surface 188 of the lockout lever 184 and no longer blocks upward movement of the lockout lever 184 based upon the urging of the spring 194 positioned between the lower surface 190 of the lockout lever 184 and the recess 196.

After the swing gate tab 182 is moved to its second position and the swing gate tab 182 is no longer holding the lockout lever 184 in its unlocked position, the firing bar 43 momentarily sits above the lockout lever 184 holding it within the recess 196. As the firing transmission assembly, in particular, the firing bar 43, is retracted, the lockout lever 184 is no longer held within the recess 196 by either the swing gate tab 182 or the firing bar 43, and the lockout lever 184 moves into a locked position under the force of the spring 194. While in this position, the lockout lever 184 will block any further attempts to activate the firing means (see FIGS. 12 and 13). Although the lockout lever 184 blocks rearward movement of the driver 131, the firing bar 43 is ultimately retracted to its proximal position. After the lockout lever 184 is released into its up position when the firing bar 43 moves to its distal position, there is a sloped surface 185 on the distal face of the lockout lever 184 which acts as a cam that allows the firing bar 43 to push it "down" out of the way during the reward retraction of the firing bar 43.

Figure 14:
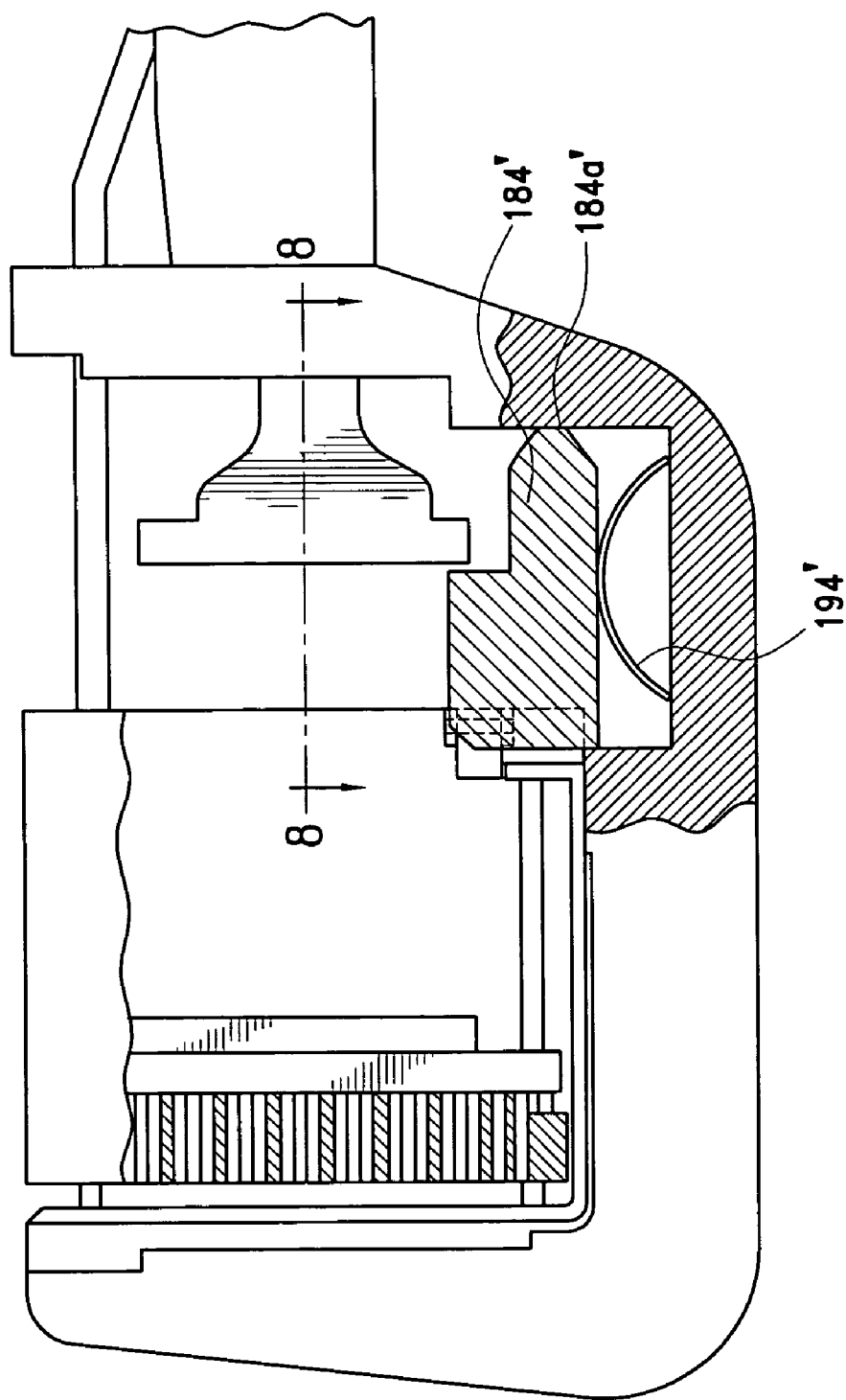
FIG. 14 is an alternate embodiment of the lockout mechanism disclosed with reference to FIGS. 6 through 13.

Referring to FIG. 14, although a linear lockout lever is disclosed in accordance with a preferred embodiment of the present invention, the lockout lever 184 could also be a rotating lockout lever 184' that is mounted at one end 184a' for pivotal rotation about the mount such that the spring biased 194' upward rotating lockout lever 184' still functions the same way as described with reference to the preferred embodiment disclosed with reference to FIGS. 6 to 13.

In accordance with a further embodiment of the present invention, and with reference to FIGS. 15, 16 and 17, the swing gate tab does not constantly sit above the lockout lever prior to firing as described above with reference to FIGS. 6 through 13. The present fired device lockout mechanism 280 employs a swing gate 282 pivotally secured to the unused cartridge module 220. In accordance with a preferred embodiment, the cartridge module 220 includes a cartridge housing 223 and the swing gate 282 is secured to a side wall 221 of the cartridge module 220. With this in mind, and as will be appreciated based upon the following disclosure, side wall 221 of the cartridge module 220 is provided with a recess 222 shaped and dimensioned to receive the swing gate 282 as it rotates toward the side wall 221 allowing the firing bar 243 to pass thereby.

The swing gate 282 is shaped and dimensioned for rotation to block further movement of the fired driver 231 and consequently prevent use of the previously fired cartridge module 220. With this in mind, the swing gate includes a front facing surface 288 having a cut out section 286 adjacent its distal end and an angled surface 289 adjacent its proximal end. A flat surface 291 is positioned between the cut out section 286 and the angled surface 289.

The pre-firing configuration of the present lockout mechanism 280 is shown with reference to FIG. 15. The cartridge module 220 is loaded with the swing gate 282 in its first position as shown. The swing gate lock 282 is maintained in its first position until the firing bar 243 moves forward and rotates the swing gate 282 to its second position, or "spent cartridge" position (see FIGS. 16, 17 and 18). The lock tab 284 sits directly behind the swing gate tab 282 and assists in keeping the swing gate 282 in its first position.

Upon firing of the firing transmission assembly, the firing bat 243 is forcefully moved forward engaging the swing gate 282, particularly, the flat surface 291 of the swing gate 282. The force of the firing bat 243 rotates the swing gate 282 with enough force to deflect the lock tab 284, allowing the swing gate 282 to be held within the recess 222 formed in the side wall 221 of the cartridge housing 223 between the lock tab 284 and the wall of the cartridge module 220. Movement of the lock tab 284 is further facilitated by the provision of a beveled surface 285 over which the swing gate 282 moves during rotation thereof and movement of the firing bar 243 relative to the swing gate is further facilitated by the angled surface 289 of the swing gate 282 over which the firing bar 243 slides as it rotates the swing gate 282.

At this position, the swing gate 282 is in its second position substantially parallel to the longitudinal axis of the linear surgical stapler. While in this second position, the cut out section 286 along the front facing surface 288 of the swing gate 282 is positioned for preventing rearward movement of the driver 231, and consequently prevents further use of the cartridge module 220.

The lockout mechanisms in accordance with the present invention overcome shortcoming of the prior art by providing a variety of advantages. In particular, the present invention prevents the driver from being pushed back in a manner turning off lockout. In addition, the present lockout mechanism is better than other lockout mechanisms as it works between the anvil structure, which is typically built for high loads, and firing bar directly to produce a stronger lockout. In addition, the driver is exposed above the cartridge deck after firing, providing a visual indicator of a spent cartridge. This provides for the possibility of adapting the lockout swing gate to lock the driver into position and prevent the user from inadvertently turning off this visual safety feature.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A linear surgical stapler adapted for applying a plurality of surgical fasteners to body tissue, the surgical stapler comprising:
   an anvil structure;
   a cartridge housing containing a plurality of surgical fasteners, the cartridge housing and anvil structure being relatively movable between a first spaced apart position and a second position in close approximation with one another;
   a firing mechanism associated with the cartridge housing for ejecting the surgical fasteners from the cartridge housing to be driven against the anvil structure; and
   a lockout mechanism interacting with the cartridge housing for selective activation and deactivation of the linear surgical stapler by blocking the firing mechanism;
   the lockout mechanism includes a swing gate tab pivotally secured to the cartridge housing such that firing of the linear surgical stapler by activation of the firing mechanism rotates the swing gate tab from a first position to a second position;
   the lockout mechanism also includes a lockout lever mounted to a supporting structure of the linear surgical stapler in which the cartridge housing is positioned for movement between an unlocked position and a locked position, wherein the lockout lever blocks movement of the firing mechanism when in the locked position, the swing gate tab holds the lockout lever in the unlocked position when the swing gate tab is in the first position and releases the lockout lever for movement to the locked position when the swing gate tab is rotated to the second position; and
   wherein firing of the linear surgical stapler rotates the swing gate tab from the first position to the second position releasing the lockout lever for movement from the unlocked position to the locked position for preventing further firing by activation of the firing mechanism of the cartridge housing after use, by blocking further activation of the firing mechanism.

2. The linear surgical stapler according to claim 1, wherein the lockout lever is spring biased.

3. The linear surgical stapler according to claim 2, wherein the lockout lever is mounted on a support frame of the linear surgical stapler adjacent the cartridge housing.

4. The linear surgical stapler according to claim 3, wherein the lockout lever sits within a recess formed in the support frame of the linear surgical stapler.

5. The linear surgical stapler according to claim 4, wherein the lockout lever includes a top surface exposed from the recess and a lower surface sitting within the recess.

6. The linear surgical stapler according to claim 5, wherein the top surface includes a tab member shaped and dimensioned for engaging the firing mechanism in a manner preventing firing of the linear surgical stapler.

7. The linear surgical stapler according to claim 1, wherein the swing gate tab is pivotally secured to the cartridge housing such that it sits above the lockout lever when it is positioned for locking of the lockout lever prior to firing of the linear surgical stapler.

8. The linear surgical stapler according to claim 1, wherein the swing gate tab moves between a first position substantially transverse to a longitudinal axis of the linear surgical stapler and a second position substantially parallel to the longitudinal axis of the linear surgical stapler, the swing gate tab sits above the lockout lever in its first position holding down the lockout lever in an unlocked position.

9. A linear surgical stapler adapted for applying a plurality of surgical fasteners to body tissue, the surgical stapler comprising:
   an anvil structure;
   a cartridge housing containing a plurality of surgical fasteners, the cartridge housing and anvil structure being relatively movable between a first spaced apart position and a second position in close approximation with one another;
   a firing mechanism movable between a retracted first position and a fired position associated with the cartridge housing for ejecting the surgical fasteners from the cartridge housing to be driven against the anvil structure; and a lockout mechanism interacting with the cartridge housing for selective activation and deactivation of the linear surgical stapler by blocking the firing mechanism;

the lockout mechanism includes a swing gate tab pivotally secured to the cartridge housing at a position preventing movement of a lockout lever mounted to a supporting structure of the linear surgical stapler in which the cartridge housing is positioned when the swing gate is in a first position, such that firing of the linear surgical stapler by actuation of the firing mechanism rotates the swing gate tab from the first position releasing the lockout lever for preventing further firing by actuation of the firing mechanism of the cartridge housing after use, blocking further activation of the firing mechanism;

wherein the swing gate tab moves between a first position substantially transverse to a longitudinal axis of the linear surgical stapler and a second position substantially parallel to the longitudinal axis of the linear surgical stapler, the swing gate tab sits above the lockout lever in its first position holding down the lockout lever in an unlocked position and wherein prior to firing of the linear surgical stapler the swing gate tab is positioned slightly forward of the lockout lever such that rotation of the swing gate tab causes the swing gate tab to come into contact with the lockout lever.

10. The linear surgical stapler according to claim 9, wherein the swing gate tab moves between a first position substantially transverse to a longitudinal axis of the linear surgical stapler and a second position substantially parallel to the longitudinal axis of the linear surgical stapler, such that when the swing gate tab is in its first position it sits forward of an upper surface of the lockout lever and during firing of the surgical stapler device the swing gate tab is rotated to its second position substantially parallel to the longitudinal axis of the surgical stapler device and removed from the upper surface of the lockout lever permitting the lockout lever to move into a locked position.

11. The linear surgical stapler according to claim 9, wherein the firing mechanism includes a firing bar and the force from the firing mechanism rotates the swing gate tab with enough force such that the firing bar deflects the lockout lever downwardly into a recess and out of the way of a firing bar and movement of the swing gate tab continues to its second position substantially parallel to the longitudinal axis of the surgical stapling device where, and once the firing mechanism is moved to its retracted position, the lockout lever returns to a blocking position preventing any further rotation of the swing gate and firing of the linear surgical stapler.

12. A linear surgical stapler adapted for applying a plurality of surgical fasteners to body tissue, the surgical stapler comprising:
an anvil structure;
a cartridge housing containing a plurality of surgical fasteners, the cartridge housing and anvil structure being relatively movable between a first spaced apart position and a second position in close approximation with one another;
a firing mechanism associated with the cartridge housing for ejecting the surgical fasteners from the cartridge housing to be driven against the anvil structure; and
a lockout mechanism interacting with the cartridge housing for selective activation and deactivation of the linear surgical stapler by blocking the firing mechanism;

the lockout mechanism including a lockout lever mounted to a supporting structure of the linear surgical stapler in which the cartridge housing is positioned, the lockout lever cooperating with a swing gate pivotally secured to the cartridge housing wherein the swing gate selectively prevents movement of the lockout lever when the swing gate is in a first position such that firing of the linear surgical stapler by actuation of the firing mechanism rotates the swing gate from the first position releasing the lockout lever for preventing further firing by actuation of the firing mechanism of the cartridge housing after use, by blocking further activation of the firing mechanism; and wherein a front facing surface of the swing gate includes a cut out section positioned for engaging a driver of the stapler and preventing further movement thereof.

13. The linear surgical stapler according to claim 12, wherein the swing gate is mounted along a side wall of the cartridge housing.

14. A linear surgical stapler adapted for applying a plurality of surgical fasteners to body tissue, the surgical stapler comprising:
an anvil structure;
a cartridge housing containing a plurality of surgical fasteners, the cartridge housing and anvil structure being relatively movable between a first spaced apart position and a second position in close approximation with one another;
a firing mechanism associated with the cartridge housing for ejecting the surgical fasteners from the cartridge housing to be driven against the anvil structure; and
a lockout mechanism interacting with the cartridge housing for selective activation and deactivation of the linear surgical stapler by blocking the firing mechanism;
the lockout mechanism includes a lockout lever mounted to a supporting structure of the linear surgical stapler in which the cartridge housing is positioned, the lockout lever cooperating with a swing gate pivotally secured to the cartridge housing wherein the swing gate selectively prevents movement of the lockout lever when the swing gate is in a first position such that firing of the linear surgical stapler by actuation of the firing mechanism rotates the swing gate from the first position releasing the lockout lever for preventing further firing by actuation of the firing mechanism of the cartridge housing after use by blocking further activation of the firing mechanism; and
the cartridge module further including a lock tab which prevents movement of the swing gate after rotation of the swing gate during firing.

15. A linear surgical stapler adapted for applying a plurality of surgical fasteners to body tissue, the surgical stapler comprising:
an anvil structure;
a cartridge housing containing a plurality of surgical fasteners, the cartridge housing and anvil structure being relatively movable between a first spaced apart position and a second position in close approximation with one another;
a firing mechanism associated with the cartridge housing for ejecting the surgical fasteners from the cartridge housing to be driven against the anvil structure, the firing mechanism including a firing bar movable between a first position and a retracted position; and
a lockout mechanism interacting with the cartridge housing for selective activation and deactivation of the linear surgical stapler by blocking the firing mechanism;

the lockout mechanism includes a swing gate tab pivotally secured to the cartridge housing at a position preventing movement of a lockout lever wherein the swing gate tab moves between a first position in which it prevents movement of the lockout lever and a second position in which the lockout lever is released for movement, such that firing of the linear surgical stapler by actuation of the firing mechanism rotates the swing gate tab releasing the lockout lever for preventing further firing of the cartridge housing after use, force from the firing mechanism rotates the swing gate tab with enough force such that the firing bar deflects the lockout lever downwardly into a recess and out of a way of the firing bar and movement of the swing gate tab continues to a second position of the swing gate substantially parallel to the longitudinal axis of the surgical stapling device where, and once the firing bar is moved to the retracted position, the lockout lever returns to a blocking position preventing any further rotation of the swing gate and firing of the linear surgical stapler.

* * * * *